United States Patent [19]

Manning et al.

[11] 4,159,545
[45] Jul. 3, 1979

[54] WORKING ARTIFICIAL HAND COMBINATION

[75] Inventors: Willie D. Manning, Bradford; Jerry Whitehead, Trenton, both of Tenn.

[73] Assignee: M-W Handicapped Enterprises, Inc., Trenton, Tenn.

[21] Appl. No.: 836,651

[22] Filed: Sep. 26, 1977

[51] Int. Cl.$^2$ .............................................. A61F 1/06
[52] U.S. Cl. ........................................................ 3/12.8
[58] Field of Search ................... 3/12.8, 12, 12.4, 12.5

[56] References Cited

U.S. PATENT DOCUMENTS

| | | | |
|---|---|---|---|
| 1,268,546 | 6/1918 | Christmann | 3/12.8 |
| 1,278,106 | 9/1918 | Caron | 3/12.8 X |
| 1,278,305 | 9/1918 | Corley | 3/12.8 |
| 1,310,589 | 7/1919 | Trautman | 3/12.8 |
| 2,030,785 | 2/1936 | Dorrance | 3/12.8 |
| 2,566,375 | 9/1951 | Rocklin | 3/12.8 |
| 3,802,302 | 4/1974 | Bengtson | 3/12.8 X |
| 4,009,496 | 3/1977 | Allen | 3/12.8 |

*Primary Examiner*—Clifford D. Crowder
*Attorney, Agent, or Firm*—Francis A. Keegan

[57] ABSTRACT

An artificial hand for operation of various implements such as tools and useful devices and the like having a pair of fingers in which one of the fingers is releasably gripped to the locking post of an implement handle attachment. The other of the pair of fingers is operable to control a trigger means to operate the implement. The implement handle atttachment includes a base and locking post protruding outwardly from the base. The post slidably receives and releasably locks the artificial hand to the post while abutment means limits the relative sliding motion and prevents movement between the post and the artificial hand when in locking engagement. The implement handle attachment also may include a finger supporting means to provide additional stability and security to the artificial hand. Trigger means may be secured to the attachment for engagement by one of the moving fingers for operation of the trigger switch on the implement. The method of adapting an artificial hand having a pair of relatively movable fingers to perform useful functions with various implements which include the steps of, inserting one of the fingers into a support proximate to the working end of the finger, inserting one of the fingers onto a locking post, locking the finger onto the locking post, supporting the artificial hand separately at one end remote from the working end and additionally at a location proximate to the working end, permitting the performance of a useful function with the implement and selectively releasing one finger from the locking post and thereafter removing the working end of one finger from the support.

66 Claims, 14 Drawing Figures

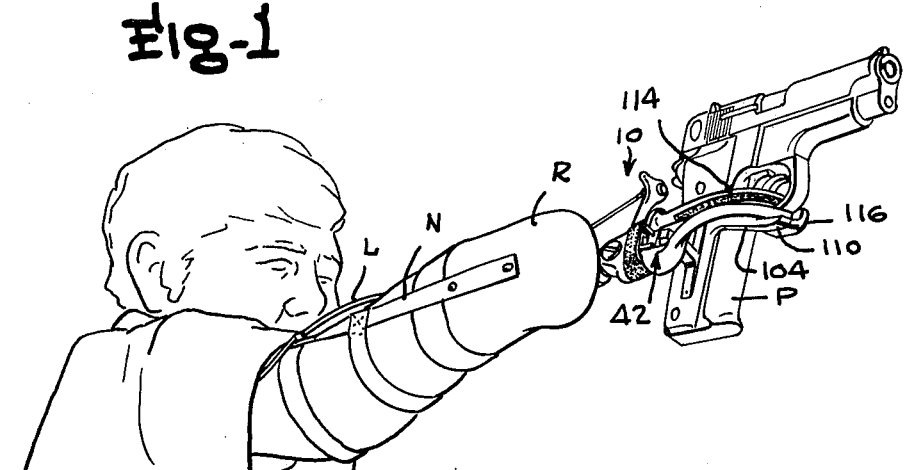
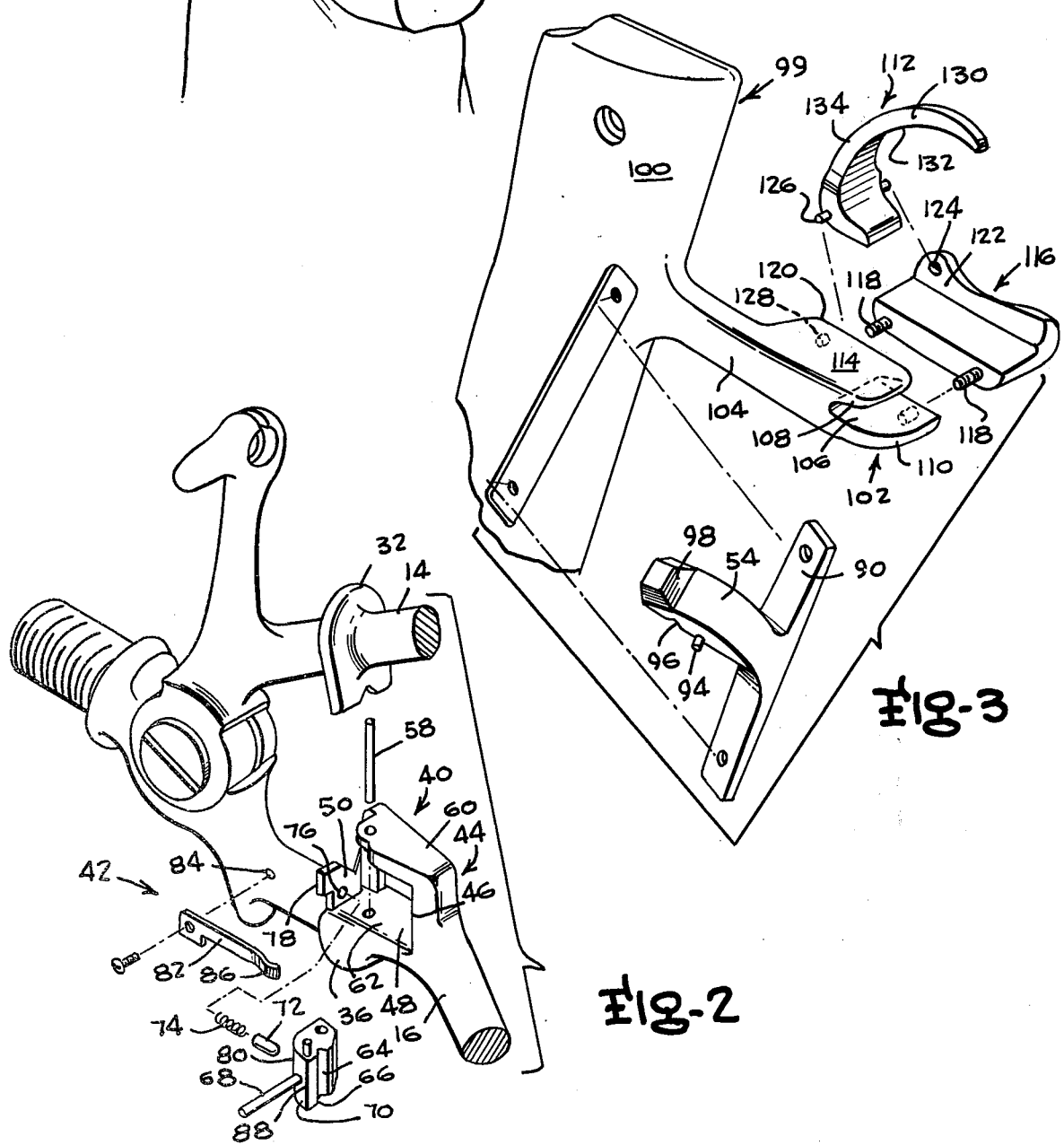

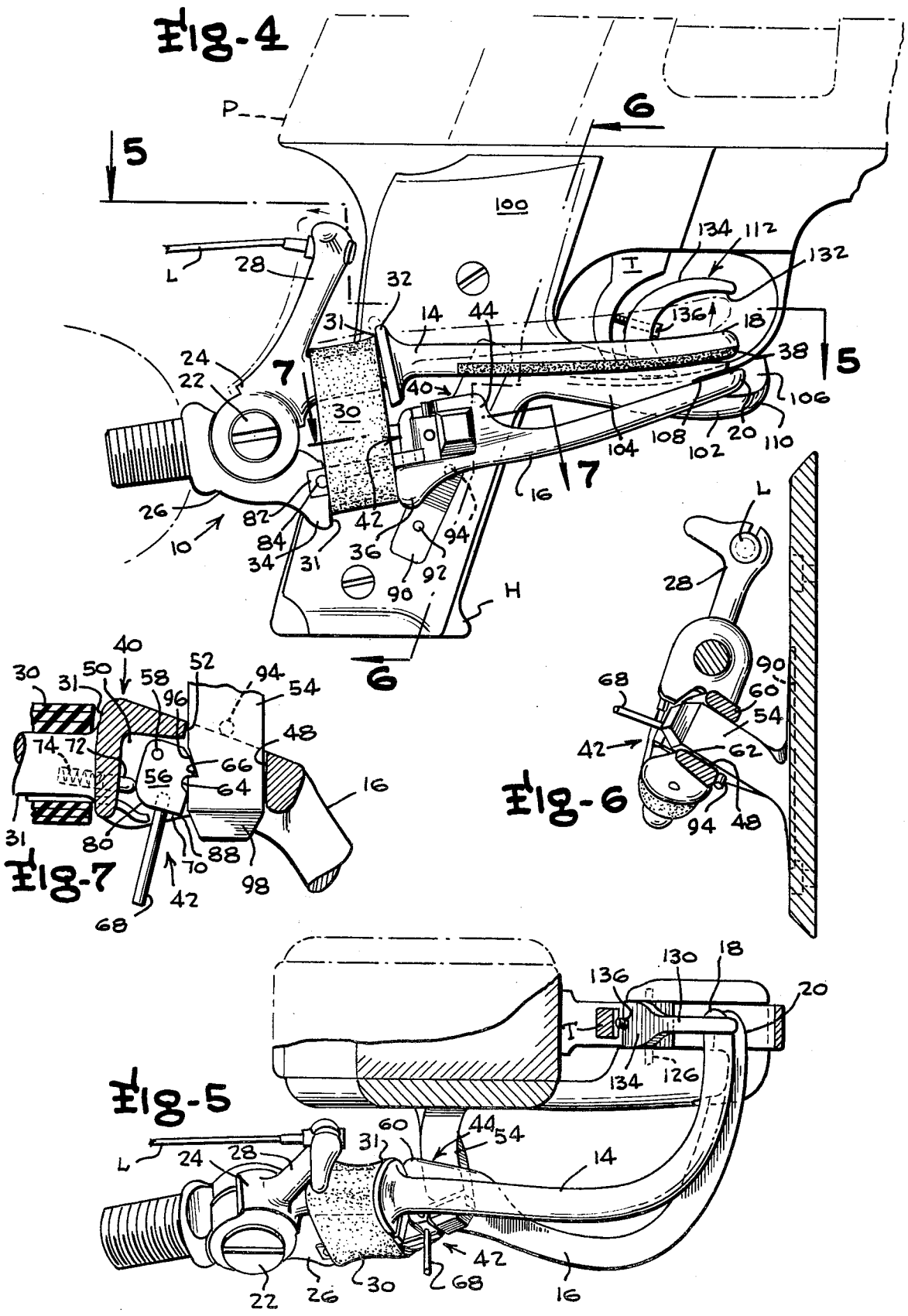

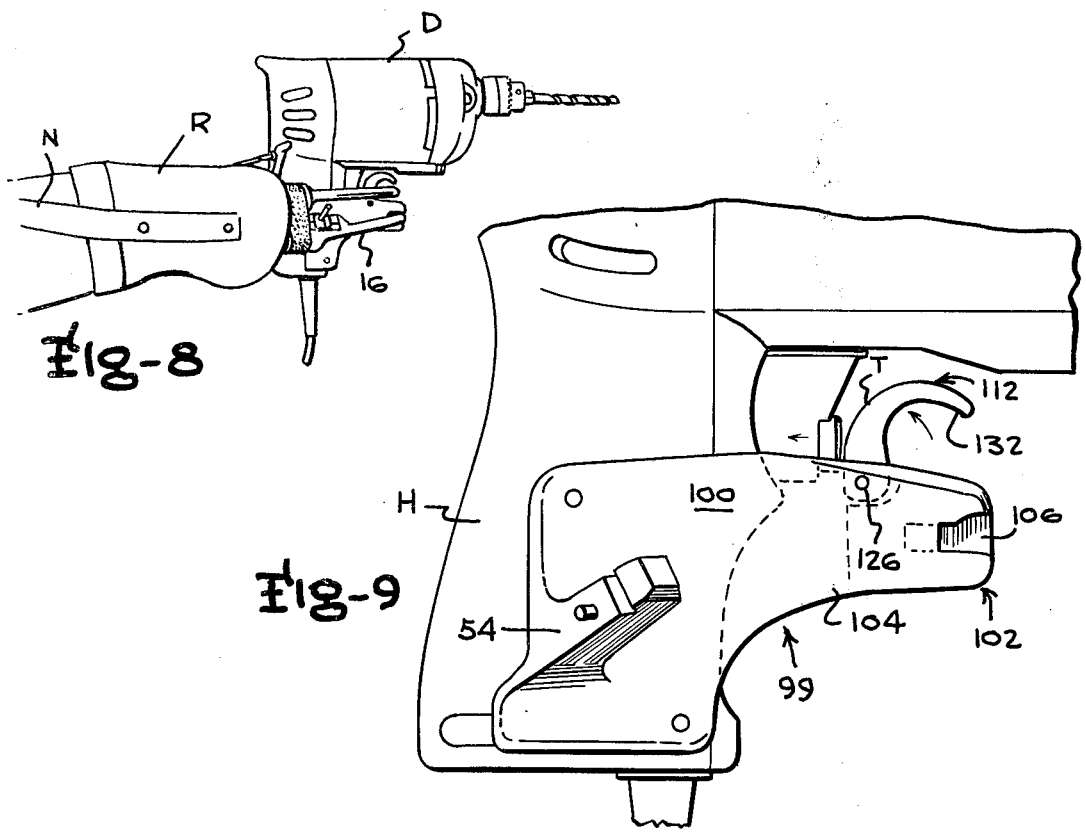
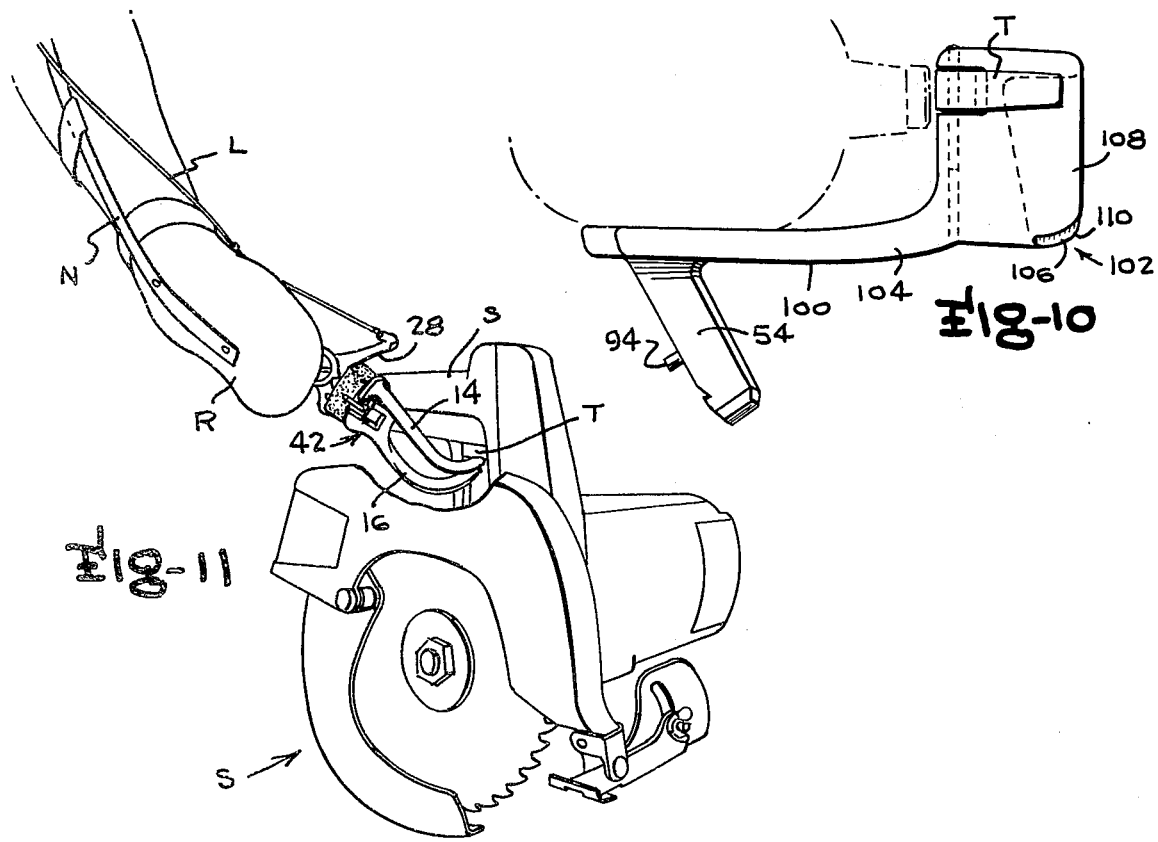

WORKING ARTIFICIAL HAND COMBINATION

BACKGROUND OF THE INVENTION

This invention relates to an artificial hand and more particularly relates to an artificial hand apparatus and method for operating various implements such as tools and other useful devices and the like. The invention is particularly useful for permitting amputees of an upper extremity or any portion thereof to engage in useful work or activity requiring grasping common tools or other devices.

Prior Art

In over four decades little effort has been exerted in the field of prosthetics for amputees who have lost the effective use their hands or fingers. At present there are over 74,000 civilian amputees with partial or total loss of the upper limb. Military amputees would add perhaps another 9,000. These individuals, based upon prior art technology, are generally unable to pursue former or new occupations requiring the use of implements such as craftsman's tools, scientific instruments, or even sporting equipment. The psychological and economic harm experienced by these otherwise healthy and willing individuals is a significant public concern.

Among the prior art devices, Dorrance U.S. Pat. No. 2,030,785 remains today the typical general arrangement of an artificial hand incorporating relatively movable hooks or fingers. The fingers are pivoted along a ball bearing supported axis and are separated by operation of the movable finger through a bell crank arrangement operated by a control line attached to the end of the bell crank. The relatively movable fingers are maintained in mutual contact or in grasping engagement by elastic bands surrounding the fingers at a point adjacent the pivot. The grasping force generated by the fingers is determined by the strength and number of the superposed elastic bands.

It has been found for instance that the support necessary to grasp securely such implements that have handles is beyond the capability of the artificial hand because pressure that may be applied to grasp any implement is limited to the force producable by the wearer to overcome the elastic bands and open the fingers. This force to overcome the bands is easily generated a few times but over the course of hours, it is very fatiguing. The result would be a loss in efficiency of operation.

The grasping of other implements to perform useful functions is limited with prior art devices particularly if the implement inherently produces a recoil, jarring or other strong reaction force that would be imparted to the artificial hand.

Experience has demonstrated that these implements having sudden reaction forces cannot be grasped effectively with the prior art artificial hands. The implements frequently become dislodged from or disoriented to the artificial hand disabling the wearer from continued use of the implement.

Numerous other patented artificial hands have been available to the amputees; however none of these is capable of securely holding a working implement and yet permit frequent and simple release of the implement as would be required with a working tool for instance.

Among other prior art devices of various types is Visel 1,111,508 disclosing an artificial arm for grasping a hammer. With such a prosthetic, the amputee would be unable for instance to operate a simple on and off switch for a rotary drill or electric saw or any trigger operated implement. The available work for an amputee using such a device would be extremely limited, if it existed at all.

Other patented devices have been available to the amputee including Mollenhour U.S. Pat. No. 2,415,145, Larsen U.S. Pat. No. 3,036,312 and LaCroix U.S. Pat. No. 2,566,215 all of which disclose an artificial hand for use with various devices.

None of the above prior art devices achieves a satisfactory gripping of a functional implement with the essential locking and releasing mechanism. Prior art devices are also generally without capability of supporting a working implement such as a tool or other useful device and at the same time perform a triggering or switching operation. These operations would be required, for instance, in the firing of a pistol or rifle, the operation of rotary drill, electric saw, paint sprayer, pneumatic hammer or any one of a great number of other craftsman tools, scientific instruments, industrial tools or sporting devices.

THE INVENTION

Objects of the Invention

The principal object of the present invention is the provision of means for the upper limb amputee to work productively in essentially any field with essentially the same skill exhibited by those using the same implements but having full use of their hands.

It is also a primary object of the present invention to provide an artificial hand for operation of various working implements by releasably gripping the implement with one of a pair of fingers independently of the other finger of the pair.

Another object of the present invention is to provide an artificial hand for operation of various implements which includes gripping means for easily releasably connecting the artificial hand to an implement.

A further object of the present invention is to provide an artificial hand for the operation of various implements which is releasably locked to the implement independent of one of a pair of fingers permitting the other finger to independently operate a trigger or switch on the implement.

Another object of the present invention is to provide an artificial hand for operation of various implements and which has a releasable mechanism for moving into and out of locking engagement with the implement.

This invention also has as a further object the provision of an implement handle attachment for use with an artificial hand, the attachment including a locking post protruding substantially outwardly from the base to lock onto the artificial hand, releasably locking means associated with the post and abutment means positioned on the post to limit sliding movement between the post and the artificial hand during insertion and prevent movement of the post and the artificial hand when in locking engagement with the post.

A further object of the present invention is to provide an implement handle attachment for use with an artificial hand having a pair of relatively movable fingers including a finger supporting means to support at least one of the fingers for stability of the artificial hand to the wearer and to better secure the artificial hand to the implement.

This invention also has as an object the provision of an implement handle attachment for use with an artificial hand having a pair of relatively movable fingers in which the attachment also includes a trigger mechanism for operation by one of the movable fingers and which trigger means is operative to engage a switch or trigger on the implement.

The invention also has as an object the provision of a method for adapting an artificial hand having a pair of relatively movable fingers to perform useful functions with various implements such as tools, useful devices and the like and includes the insertion of one of the fingers into locking posts on the implement, releasably locking the fingers to the locking post and inserting at least one of the fingers into a support for stability and security purposes and thereafter releasing one finger from the locking post and removing the working end of the working finger from the support.

This invention also has as an object the method of adapting an artificial hand having a pair of relatively movable fingers which includes the step of releasably locking one of the fingers to a locking post on the implement and moving the other finger independently to operate a trigger or switch on the implement independently of the locked finger.

These and other objects become apparent on a careful reading of the specification, claims, and accompanying drawings.

THE DRAWINGS

FIG. 1 is a perspective view of the artificial hand of the present invention supporting and operating a pistol for firing.

FIG. 2 is an exploded view, partly broken away, of the gripping means of the present invention and the detent forming the releasable means.

FIG. 3 is a exploded perspective view partly broken away of the implement handle attachment for use with the artificial hand of the present invention and illustrating the trigger mechanism.

FIG. 4 is a side elevational view of the artificial hand and a pistol handle attachment with the pistol in phantom lines, partly broken away, and also illustrating the operation of the trigger of the pistol by the trigger means on the implement handle attachment.

FIG. 5 is a perspective view taken along lines 5—5 of FIG. 4 illustrating the operation of the trigger means on the implement handle attachment and the trigger on the pistol.

FIG. 6 is a cross-sectional view taken along lines 6—6 of FIG. 4 illustrating the locking post and the abutment means positioned on the post to limit the relative sliding motion between the locking post and the artificial hand.

FIG. 7 is a cross-sectional view taken along the lines 7—7 of FIG. 4 illustrating the locking and releasable means in the form of a resiliently urged detent.

FIG. 8 is a perspective view of the operation of an electric rotary drill by means of the artificial hand and the handle attachment of the present invention.

FIG. 9 is a perspective view, partly broken away, of the implement handle attachment for a conventional electric drill such as shown in FIG. 8.

FIG. 10 is a top plan view of the electric drill handle attachment shown in FIG. 9.

FIG. 11 is a perspective view of the artificial hand apparatus combination operating an electric saw.

SUMMARY OF THE INVENTION

Figure 12:
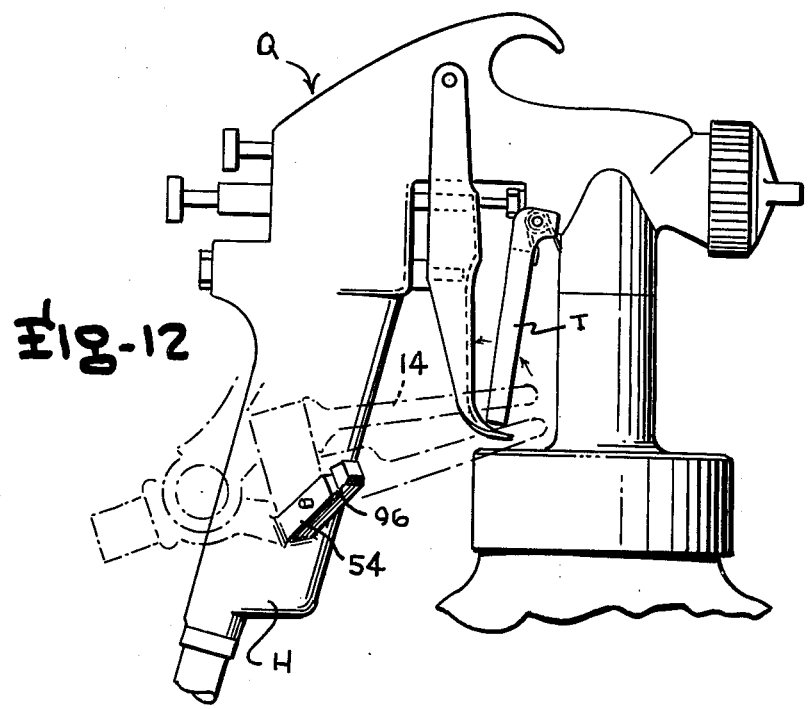
FIG. 12 is a side elevational view, partly broken away, and, partly in phantom, illustrating a paint sprayer handle attachment for the artificial hand of the present invention and illustrating the operation of the trigger on the paint sprayer.

The present invention is an artificial hand for operation of various implements such as tools and useful devices and the like having a pair of fingers in which one of the fingers is releasably gripped to an implement handle attachment. One of the pair of fingers not utilized to hold the artificial hand to a gripping post on a implement handle attachment is operable to control a trigger means to operate the implement.

An implement handle attachment is utilized for securing to the implement handle and is used with the artificial hand having a pair of relatively movable fingers. The implement handle attachment includes a base and locking post protruding outwardly from the base. The post slidably receives and releasably locks the artificial hand to the post while abutment means limits the relative sliding motion and prevents movement between the post and the artificial hand when in locking engagement. The implement handle attachment also may include a finger supporting means to provide additional stability and security to the artificial hand locked onto the locking post of the implement handle attachment. Trigger means may be secured to the attachment for engagement by one of the moving fingers for operation of the trigger switch on the implement.

The method of adapting an artificial hand having a pair of relatively movable fingers to perform useful functions with various implements which include the steps of inserting one of the fingers onto a locking post, locking the finger onto the locking post, prior to inserting the finger onto the post one of the fingers may be inserted into a support proximate to the working end of the finger, supporting the artificial hand separately at one end remote from the working end and additionally at a location proximate to the working end, permitting the performance of a useful function with the implement and selectively releasing one finger from the locking post and thereafter removing the working end of one finger from the support.

DESCRIPTION OF THE PREFERRED EMBODIMENT

In FIGS. 1, 2, 4 and 5 particularly, there is illustrated the artificial hand, generally designated 10 and forming a part of the present invention. The artificial hand 10 includes a stump receptacle R adapted to receive and encase the remaining portion of the limb. A conventional arm and shoulder harness is partially shown in FIG. 1 for holding the receptacle R in place. Operating line L is secured to the shoulder and operates artificial hand 10 in conventional manner.

Secured to the receptacle R in a suitable fashion as by threads 12 is the artificial hand shown generally at 10. The artificial hand 10 includes a pair of fingers 14 and 16 which are elongated and terminate in working tip ends 18 and 20. The fingers 14 and 16 are pivoted in conventional fashion by ball bearing pivot 22 to which the shanks 24 and 26 are connected for relative movement of the working tips 18 and 20 toward and away from each other. Bell crank arm 28 is operative to pivot finger 14 away from finger 16 in the manner shown in the phantom lines in FIG. 4. Suitable elastic bands 30 that may be of rubber or some other material are secured around the fingers 14 and 16 in the grooves 31 provided by shoulder 32 and bell crank arm 28 for the pivoting finger 14 and opposed shoulders 34 and 36 on the stationary finger 16. Resilient friction surface 38 may be secured to one or both of the inside facing surfaces of the fingers.

Up to this point the artificial hand as described is conventional in construction and in its operation. The present invention, however, departs from the prior art in providing a unique gripping means 40, as best shown in FIGS. 2 and 4. Additionally, the artificial hand of the present invention includes, a unique releasable means shown generally at 42 in combination with the gripping means 40.

In the exploded view of FIG. 2 it can be seen that the gripping means 40 is formed from an enlargement or boss 44 extending from inside toward the shank end of the finger 16 adjacent the shoulder 36. As shown, the boss 44 includes a non-round opening 46 forming a positioning means which as shown may be rectangular in shape. The opening 46 extends through the boss 44 and preferably extends between the fingers 14 and 16 without, as best shown in FIG. 4, contacting the movable finger 14. The location of the boss 44 and therefore the opening 46 is not critical and may be placed on any location along the finger 16. Ideally, however, the boss location should be remote from the working end 20 and proximate to the pivot 22 in a manner that approximates the apparent location of the palm of a normal hand. In such location the wearer will have a sense of better control to permit ease of operation of the artificial hand.

The opening 46 within the boss 44 is preferably provided with smooth surfaces 48 forming a slide means on at least several sides of the opening. As best shown in FIGS. 2 and 7 the rear portion of the boss 44 may be cut away as shown at 50 to accommodate the releasable means 42. The cutaway portion retains a surface 52 in the opening 46 to cooperate with the surfaces 48 to receive slidably the locking post 54.

Positioned within the cutaway portion 50 of the boss 44 is the releasable means 42 in the form of a detent or pawl 56. As shown in FIGS. 2 and 7, the detent is pivoted about an axis provided by pivot pin 58 which is suitably secured within the side walls 60 and 62 forming the boss 44. The pivot axis provided by the pivot pin 58 for the detent 56 is eccentrically located to permit the detent or pawl 56 to rock forwardly and rearwardly into and out of engagement with the locking post 54. The detent or pawl 56 is provided with a notch 64 and a tooth 66 to dog the locking post 54.

The detent 56 is operable into and out of engagement with the locking post 54 by means of the lever 68 position on the upper surface 70 of the detent. The detent is resiliently urged forwardly into locking engagement with locking post 54 by abutment slide 72. Suitable spring 74 is provided in an accommodating bore 76 positioned in the rear wall 78 forming a part of the shoulder 36. The abutment slide 72 contacts the rear surface 80 of the detent 56 which is suitably curved to accommodate the abutment contact of the slide 72.

It has been found desirable to also include a catch 82 secured at 84 to the shank of the finger 16. The catch 82 is an elongated flat spring steel member having a curved lip 86 which cooperates with the leading edge 88 of the detent 56 to hold the detent in released or unlocked position. The action of the catch 82 is to apply sufficient force upon the detent 56 while acting through a greater distance from the pivot point 58 in order to overcome the urging of abutment slide 72 which is to move the detent 56 into locking engagement with locking post 54. The manual control provided by the lever 68 is such that the action of both the abutment slide 72 and the catch 82 can be easily overcome to rock the detent 56 forwardly or rearwardly to lock or unlock the artificial hand and the locking post 54.

The locking post 54, best shown in FIGS. 3, 6 and 9 is supported on a base 90 which conforms to handle H of the implement. It should be quite apparent that the base 90 would be shaped in any convenient manner to conform to the handle of the implement as shown in FIGS. 3 and 6. For instance, the base 90 is secured by conventional means such as screws 92 to the handle of the implement or may become an integral part of the handle and serve the purpose of a stock plate. This construction is suitable for the pistol P of FIG. 4, the drill D of FIGS. 8 and 9, the saw S of FIG. 11 or the paint sprayer Q of FIG. 12.

Figure 14:
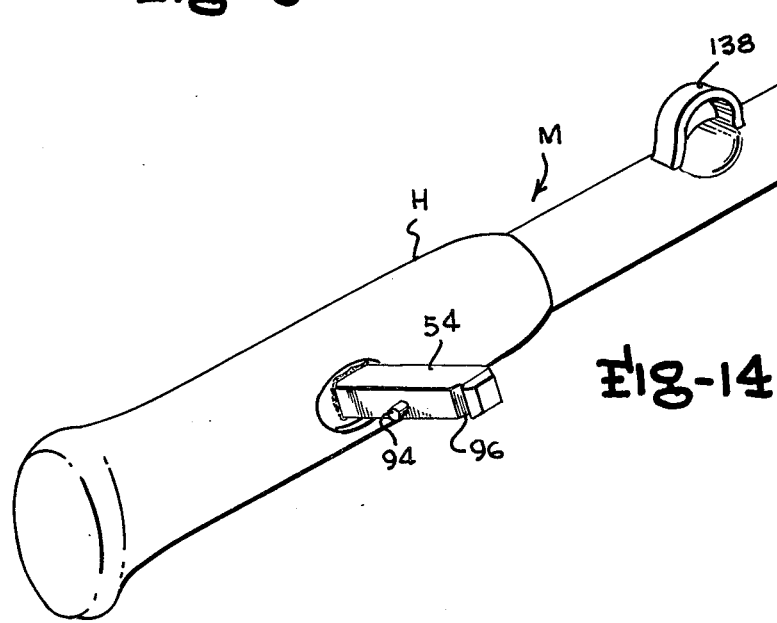
FIG. 14 is a perspective view, partly broken away, illustrating the hammer handle attachment in the form of a locking post and the finger supporting means on the hammer for receiving one of the fingers of the artificial hand.

The locking post 54 may also be made integral with the handle of the hammer M as shown in FIG. 14. Regardless of the support provided for the locking post 54 and irrespective of the type of handle or implement utilized the function of the locking post will remain the same to hold the artificial hand in a releasably secure position.

The relationship between the locking post and the artificial hand is one in which there preferably is no relative movement between them. It is for this reason, that the opening 46 and the locking post 54 have a complementary non-round or rectangular shape.

The locking post 54 is preferably sufficiently long to extend from the base 90 upwardly through and slidably engaging the gripping means 40 of the artificial hand. The complementary shape of the locking post permits sliding relationship between the opening 46 and surfaces 48 and 52 to position properly the artificial hand before operation of the implement.

The locking post 54 is provided with an abutment pin 94 to limit the relative sliding motion between the locking post and the artificial hand during insertion of the hand into the locking post. As best shown in FIG. 7, the complementary notch 96 having a ledge 97 is provided in one of the faces of the locking post 54 to receive the tooth 66 and therefore lock the gripping means to locking post. The abutment pin, the notch and the shaped sides of the locking post 54 serve to prevent movement between the post and the artificial hand when the artificial hand and its gripping means is in locking engagement with the post. The upper surface of the locking post 98 may be chamfered in order to facilitate insertion of the gripping means onto the locking post.

The locking post as shown has an angular relationship to the base or to the handle of the implement. This angle is not critical, however, without such angular relationship the wearer of the artificial hand experiences difficulty in achieving the otherwise awkward positioning of the artificial hand to lock onto the locking post. This is particularly true when the wearer seeks to retain effective use of the working ends of the fingers such as in the event that the trigger or the switch on the implement is to be operated.

It is possible, however, that the locking post may be rotatable in its base 90 such as if the locking post were provided on a steering wheel or window lift in such case the locking post would be able to rotate at its base. There are numerous possibilities to which the present invention may be directed but principally, it is intended that the present invention provide a means for the amputee to work productively with the same skill maintained by those using tools and implements and having full use of their limbs.

The handle attachment 99 for those implements requiring a stable grip to prevent twisting of the artificial hand on the stump of the amputee as well as being sufficiently secure to hold the artificial hand to the implement, is typically shown in FIG. 3. The handle attachment for the implement may include the base platform 100 or simply the base 90. To obtain the stability and security desired, it is preferable that the implement handle attachment generally referred to as 99 includes a finger supporting means 102.

The finger supporting means 102 attached by arm 104 to the handle attachment 99 or to the platform 100 which also supports the base 90. The arm 104 extends outwardly from the handle attachment in generally a transverse direction from the proximate axis of the locking post as best shown in FIGS. 3, 4 and 5. The finger supporting means 102 includes a curved groove 106 formed by facing lips 108 and 110 which are spaced sufficiently to receive the stationary finger 16 as shown in FIG. 4. The base of the groove 106 is shaped to the configuration of the concave portion of the working end of the fingers.

The arm 104 is elongated outwardly to so position the finger supporting groove 106 that it will be able to receive the curved working end 20 of the stationary finger 16. In this manner, the combination of the locking post 54 and the finger supporting means 102 together provide a dual support feature for the artificial hand. This dual support provides the stability to prevent the artificial hand from twisting or turning on the wearer and also the security to prevent the implement, such as a pistol, from being dislodged or disoriented in relationship to the artificial hand. Also an important optional feature of the present invention is the incorporation of the trigger mechanism 112.

As best shown in FIG. 3 the arm 104 is enlarged and flattened as shown at 114 not only to form the duckbill shaped curved groove 106 for receiving the finger but also to provide a location for the positioning of the trigger mount 116 secured by suitable screws 118 into the side 120 of the arm transverse to the axis of the groove 106. Trigger mount 116 includes an upstanding ledge 122 into which at one end is formed the bore 124 for receiving the trigger pivot pin 126. The other end of the pivot pin 126 is received into a complementary bore 128 in the side 120.

The trigger 130 is eccentrically mounted on the pivot pin 126 and includes an elongated concave surface 132 and an external convex surface 134. The convex surface 134 may be provided with abutment screw 136 as shown in FIG. 4 to contact the trigger T of the pistol P or may be omitted if the abutting convex surface 134 has sufficient swinging movement to contact the trigger, as for instance may be case with the electric drill, as shown in FIGS. 8 and 9.

In operation the movable finger 14, as it separates from the stationary finger 16, engages the concave surface 134 and rides upwardly along the elongated surface 132 to pivot the trigger 130 rearwardly to enable the convex surface 134 to contact the trigger or switch on any implement to which the present invention is attached.

The modifications of 8, 9 and 10 illustrate the present invention used in electric drill D in which the handle attachment for the drill is adapted to fit the handle H of the drill. The handle attachment is otherwise as described for use with pistol P.

In FIG. 11, the present invention is illustrated as being applied to an electric saw S in which the operation would be similar to operate the trigger T of the saw.

In FIG. 12, the modification illustrates the locking post 54 being integral with the handle H of the paint sprayer Q but for illustration purposes, the finger supporting means is not utilized and permits the trigger T to be operated by the movable finger 14.

Figure 13:
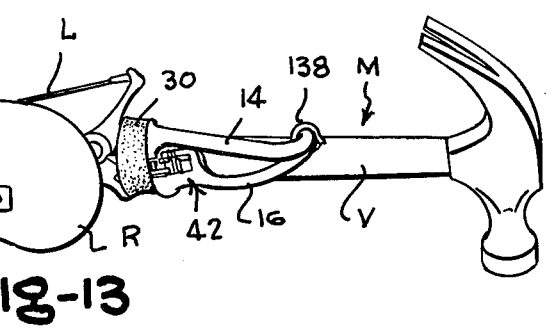
FIG. 13 is a perspective view of the apparatus combination in position for operation of a craftsman hammer.

FIGS. 13 and 14 illustrate the utilization of the invention with the hammer in which the locking post is securely positioned on the handle H of the hammer M and the finger supporting means is positioned on the shaft V of the hammer. The finger supporting means includes essentially an eyelet 138 to receive both of the fingers as best shown in FIG. 13. In this manner the hammer is securely positioned and stabilized in the artificial hand. There is no need for the triggering operation and hence both fingers are able to be positioned within the eyelet forming the finger supporting means.

In the method of the present invention the wearer of the artificial hand inserts the gripping means 40 onto the locking post 54 which is at a location remote from the working end 20 of the finger 16. The finger may be locked onto the locking post by mating of the detent 56 with the locking post and in particular both the tooth 66 into the notch 96 on the locking post and the ledge 97 of the notch 96 into the notch 64 of the detent. This secure engagement is more than adequate to hold the gripping means to the locking post and therefore the artificial hand. Should there be a finger supporting means such as 102, the stationary finger may be inserted initially to aid guiding the gripping means onto the locking post.

When in position the artificial hand is supported by either the locking post alone or preferably, additionally by the finger held in the finger supporting means 102. The complementary shaped groove 102 and the concave finger enhance this support. With such support and stability, the artificial hand is secured to the wearer and to the implement which permits the wearer to perform a useful function with the implement. Thereafter the artificial hand may be released by operation of the lever 68 which withdraws the tooth 66 from the notch 64 of the locking post. Upon release of the gripping means from the locking post, the artificial hand may be removed and the working end of the stationary finger removed from the finger supporting means.

In the manner described it should be apparent that the objects of the present invention are achieved and particularly the amputee is enabled to work productively and feel useful again.

We claim:

1. In an artificial hand for operation of various implements such as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
positioning means in the form of an opening having slide means connected there to for slidably receiving said implement,
said positioning means being secured to one of the fingers to hold the implement in preselected position independent of said other finger and located more closely adjacent to said pivot than the working end of said fingers, and
locking means connected to said positioning means for releasably locking said implement to said positioning means.

2. The artificial hand of claim 1 including,
said locking means comprising an operable detent for securing said implement to said positioning means.

3. The artificial hand of claim 2 including,
resilient means operative upon said dentent to continuously urge said detent into engagement with said implement.

4. The artificial hand of claim 1 including,
said positioning means being secured to a stationary finger.

5. The artificial hand of claim 4 including,
said gripping means being positioned between said fingers remote from the working end of said fingers.

6. The artificial hand of claim 4 including,
said locking means comprising an operable detent for securing said implement to said positioning means.

7. The artificial hand of claim 6 including,
resilient means operative upon said detent to continuously urge said detent into engagement with said implement.

8. The artificial hand of claim 1 including,
said positioning means formed from a boss secured to one of said fingers.

9. The artificial hand of claim 8 including,
said boss including said opening for releasably securing said implement.

10. In an artificial hand for operation of various implements such as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
gripping means secured to one of the fingers to hold the implement in preselected position independent of said other finger,
releasable means connected to said gripping means for releasably connecting said implement to said gripping means and
said gripping means being positioned between said fingers remote from the working end of said fingers.

11. In an artificial hand for operation of various implements sch as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
gripping means secured to one of the fingers to hold the implement in preselected position independent of said other finger,
releasable means connected to said gripping means for releasably connecting said implement to said gripping means and
said releasable means including a detent and an eccentric pivot for said detent to rock said detent into and out of engagement with said implement.

12. In an artificial hand for operation of various implements such as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
gripping means secured to one of the fingers to hold the implement in preselected position independent of said other finger,
releasable means connected to said gripping means for releasably connecting said implement to said gripping means,
said releasable means comprising an operable detent for securing said implement to said gripping means and
a lever positioned on said detent extending upwardly for manual manipulation of said detent to control the selective releasing of said implement.

13. In an artificial hand for operation of various implements such as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
gripping means secured to one of the fingers to hold the implement in preselected position independent of said other finger,
releasable means connected to said gripping means for releasably connecting said implement to said gripping means,
said gripping means being secured to a stationary finger and
said releasable means including a detent and an eccentric pivot for said detent to rock said detent into and out of engagement with said implement.

14. In an artificial hand for operation of various implements such as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising,
gripping means secured to one of the fingers to hold the implement in preselected position independent of said other finger,
releasable means connected to said gripping means for releasably connecting said implement to said gripping means
said gripping means being secured to a stationary finger,
said releasable means comprising an operable detent for securing said implement to said gripping means and
a lever positioned on said detent extending upwardly for manual manipulation of said detent to control the selective releasing of said implement.

15. In an artificial hand for operation of various implements as tools and useful devices and the like, having a pair of fingers including facing gripping surfaces extending from a pivot for movement into and out of engagement, tensioning means engaging the fingers to urge movement of the fingers toward such engagement, means selectively operated by the wearer to open and close the fingers, the improvement comprising, gripping means secured to one of the fingers to hold the implement in preselected position independent of said other finger, releasable means connected to said gripping means for releasably connecting said implement to said gripping means and said gripping means formed from a boss secured to one of said fingers and said boss being positioned to face said opposite finger.

16. The artificial hand of claim 15 including said gripping means being secured to a stationary finger.

17. The artificial hand of claim 16 including, said releasable means comprising an operable detent for securing said implement to said gripping means.

18. The artificial hand of claim 17 including, resilient means operative upon said detent to continuously urge said detent into engagement with said implement.

19. The artificial hand of claim 17 including, a lever positioned on said detent extending upwardly for manual manipulation of said detent to control the selective releasing of said implement.

20. The artificial hand of claim 15 including, said releasable means including a detent and an eccentric pivot for said detent to rock said detent into and out of engagement with said implement.

21. The artificial hand of claim 15 including, resilient means operative upon said detent to continuously urge said detent into engagement with said implement, said releasable means including a detent, an eccentric pivot for said detent to rock said detent into and out of engagement with said implement, and a lever positioned on said detent extending upwardly for manual manipulation of said detent to control the selective releasing of said implement.

22. An implement handle attachment for use with an artificial hand having a pair of relatively movable fingers, said attachment comprising, a base shaped to be positioned upon the implement handle, securing means for attaching said base to said implement handle, a locking post protruding substantially outwardly from said base to a length sufficient to lock onto said artificial hand, means positioned on said post for slidably receiving and releasably locking said artificial hand to said post, abutment means positioned on said post to limit the relative sliding motion between the locking post and the artificial hand during insertion of said hand onto said locking post and prevent movement between said post and said artificial hand when in locking engagement with said post.

23. The implement handle attachment of claim 22 including finger supporting means associated with said handle attachment and located remote from said locking post.

24. The implement handle attachment of claim 23 including said finger supporting means being located at a distance from said locking post equal to the distance between the locking post and the approximate end of the finger during locking engagement.

25. The implement handle attachment of claim 23 including, an arm secured to said base at one end and extending outwardly generally transversely to said locking post at the other end, said other end forming said finger supporting means.

26. The implement handle attachment of claim 23 including, said finger supporting means comprising holding means to receive one of said fingers for stationary engagement relative to said locking post.

27. The implement handle attachment of claim 26 including, said finger supporting means holding a stationary one of said fingers and permitting free movement of said other of said pair of fingers.

28. The implement handle attachment of claim 23 including said finger supporting means including a groove to hold said finger.

29. The implement handle attachment of claim 22 including, finger supporting means associated with said handle attachment and located remote from said locking post, said finger supporting means being located at a distance from said locking post equal to the distance between the locking post and the approximate end of the finger during locking engagement, an arm secured to said base at one end and extending outwardly generally transversely to said locking post at the other end, said other end forming said finger supporting means.

30. The implement handle attachment of claim 22 including, finger supporting means associated with said handle attachment and located remote from said locking post, said finger supporting means being located at a distance from said locking post equal to the distance between the locking post and the approximate end of the finger during locking engagement, an arm secured to said base at one end and extending outwardly generally transversely to said locking post at the other end, said other end forming said finger supporting means, said finger supporting means comprising holding means to receive one of said fingers for stationary engagement relative to said locking post, said finger supporting means holding a stationary one of said fingers and permitting free movement of said other of said pair of fingers.

31. The implement handle attachment of claim 22 including, trigger means secured to said attachment for engagement by one of said moving fingers for operation of the implement having the handle.

32. The implement handle attachment of claim 31 including, said trigger means including a curved arm having a concave inside surface for contact with said moving finger.

33. The implement handle attachment of claim 32 including,
said curved arm being pivoted at one end.

34. The implement handle attachment of claim 32 including,
said concave surface being of sufficient length to slidably engage said moving finger for the full period of movement of said finger.

35. The implement handle attachment of claim 31 including,
abutment means on one side of said trigger means for actuating said implement.

36. The implement handle attachment of claim 35 including,
said abutment means being a convex surface for sliding contact with and for operation of said implement.

37. The implement handle attachment of claim 31 including,
said trigger means including a curved arm having a concave inside surface for contact with said moving finger,
abutment means on one side of said trigger means for actuating said implement.

38. The implement handle attachment of claim 31 including,
said trigger means including a curved arm having a concave inside surface for contact with said moving finger,
abutment means on one side of said trigger means for actuating said implement, and
said curved arm being pivoted at one end.

39. The implement handle attachment of claim 31 including,
said trigger means including a curved arm having a concave inside surface for contact with said moving finger,
abutment means on one side of said trigger means for actuating said implement,
said curved arm being pivoted at one end, and 40. In an apparatus combination for adaption of an artificial hand to perform useful functions with various implements such as tools, useful devices and the like, said artificial hand having, a pair of fingers having facing gripping surfaces extending from a pivot for movement into and out of engagement, tensioning means engaging the fingers to urge movement of the fingers toward such engagement means selectively operated by the wearer to open and close the fingers, the improvement comprising,
gripping means secured to the end of the fingers to hold the implement in preselected position independent of said other finger,
releasable means connected to said gripping means for releasably connecting said implement to said gripping means, and in combination the improvement further comprising,
an attachment to the handle of said implement for locking engagement with said artificial hand,
said attachment having a base shaped to conform in part to the implement handle,
securing means for attaching said base to said implement handle,
a locking post protruding substantially outwardly from said base to a length sufficient to lock onto said artificial hand, and
means positioned on said post for slidably receiving and releasably locking said artificial hand to said post.

41. The apparatus combination of claim 40 including,
abutment means positioned on said post to limit the relative sliding motion between the locking post and the artificial hand during insertion of said hand onto said locking post and prevent movement between said post and said artificial hand when in locking engagement with said post.

42. The apparatus combination of claim 41 including,
means located on said post for preventing relative movement between said post and said artificial hand when in locking engagement with said post.

43. The apparatus combination of claim 40 including,
said releasable means comprising an operable detent for securing said implement to said gripping means.

44. The apparatus combination of claim 43 including,
a lever positioned on said detent extending upwardly for manual manipulation of said detent to control the selective releasing of said implement.

45. The apparatus combination of claim 40 including,
said releasable means including a detent and an eccentric pivot for said detent to rock said detent into and out of engagement with said implement.

46. The apparatus combination of claim 40 including
said gripping means being positioned between said fingers remote from the working end of said fingers,
said releasable means comprising an operable detent for securing said implement to said gripping means
resilient means operative upon said detent to continuously urge said detent into engagement with said implement,
said releasable means including a detent, an eccentric pivot for said detent to rock said detent into and out of engagement with said implement, and
a lever positioned on said detent extending upwardly for manual manipulation of said detent to control the selective releasing of said implement.

47. The apparatus combination of claim 40 including,
said gripping means formed from a boss secured to one of said fingers, and
said boss including an opening for releasably securing said implement.

48. The apparatus combination of claim 40
said boss being positioned to face said opposite finger.

49. The apparatus combination of claim 40 including,
finger supporting means associated with said handle attachment and located remote from said locking post.

50. The apparatus combination of claim 49 including
said finger supporting means being located at a distance from said locking post equal to the distance between the locking post and the approximate end of the finger during locking engagement.

51. The apparatus combination of claim 49 including,
an arm secured to said base at one end and extending outwardly generally transversely to said locking post at the other end, said other end forming said finger supporting means.

52. The apparatus combination of claim 49 including
said finger supporting means comprising holding means to receive one of said fingers for stationary engagement relative to said locking post.

53. The apparatus combination of claim 52 including, said finger supporting means holding a stationary one of said fingers and permitting free movement of said other of said pair of fingers.

54. The apparatus combination of claim 49 including, finger supporting means associated with said handle attachment and located remote from said locking post,
said finger supporting means being located at a distance from said locking post equal to the distance between the locking post and the approximate end of the finger during locking engagement,
an arm secured to said base at one end and extending outwardly generally transversely to said locking post at the other end, said other end forming said finger supporting means,
said finger supporting means comprising holding means to receive one of said fingers for stationary engagement relative to said locking post, and
said finger supporting means holding a stationary one of said fingers and permitting free movement of said other of said pair of fingers.

55. The apparatus combination of claim 40 including, trigger means secured to said attachment for engagement by one of said moving fingers for operation of the implement having the handle.

56. The apparatus combination of claim 40 including, trigger means secured to said attachment for engagement by one of said moving fingers for operation of the implement having the handle, and
said trigger means including a curved arm having a concave inside surface for contact with said moving finger.

57. The apparatus combination of claim 40 including, trigger means secured to said attachment for engagement by one of said moving fingers for operation of the implement having the handle, and
said trigger means including a curved arm having a concave inside surface for contact with said moving finger.

58. The apparatus combination of claim 40 including, trigger means secured to said attachment for engagement by one of said moving fingers for operation of the implement having the handle,
said trigger means including a curved arm having a concave inside surface for contact with said moving finger,
abutment means on one side of said trigger means for actuating said implement.

59. The apparatus combination of claim 40 including, trigger means secured to said attachment for engagement by one of said moving fingers for operation of the implement having the handle,
said trigger means including a curved arm having a concave inside surface for contact with said moving finger,
abutment means on one side of said trigger means for actuating said implement, and
said curved arm being pivoted at one end.

60. The apparatus combination of claim 40 including, trigger means secured to said attachment for engagement by one of said moving fingers for operation of the implement having the handle,
said trigger means including a curved arm having a concave inside surface for contact with said moving finger,
abutment means on one side of said trigger means for actuating said implement,
said curved arm being pivoted at one end, and
said concave surface being of sufficient length to slidably engage said moving finger for the full period of movement of said finger.

61. The method of adapting an artificial hand having a pair of relatively movable fingers to perform useful functions with various implements such as tools, useful devices and the like comprising:
inserting at least one of said fingers into a support as located on said implement proximate to the working end of said finger,
inserting one of said fingers onto a locking post on said implement at a location on said finger remote from a working end of said finger,
locking said one finger to said locking post, to prevent relative movement between said one finger and said locking post,
supporting said artificial hand separately at one end of one of said fingers remote from the working end and additionally at a location proximate to said working end to stabilize the artificial hand to the wearer and secure the artificial hand to the implement,
permitting the performing of a useful function with said implement locked to said artificial hand,
selectively releasing said one finger from said locking post, and thereafter
removing said working end of said one finger from said support.

62. The method of claim 61 including
inserting said one finger, said one finger being stationary, into said support independent of said other finger,
relatively moving said other finger to permit said insertion of said stationary finger.

63. The method of claim 61 including,
inserting said one finger onto said locking post at a location between said fingers.

64. The method of claim 61 including,
moving said other finger to operate a trigger on said implement independently of said stationary finger while supporting said implement with said stationary finger.

65. The method of claim 61 including
said one finger inserted onto said locking post being stationary, inserting said stationary finger into said support independent of said other finger,
relatively moving said other finger to permit said insertion of said stationary finger,
moving said other finger to operate a trigger on said implement independently of said stationary finger while supporting said implement with said stationary finger.

66. The method of claim 61 including,
inserting a stationary finger onto said locking post and inserting said stationary finger into said support independent of said other finger,
relatively moving said other finger to permit said insertion of said stationary finger,
inserting said one finger onto said locking post at a location between said fingers,
moving said other finger to operate a trigger on said implement independently of said stationary finger while supporting said implement with said stationary finger.

* * * * *